US006586233B2

(12) United States Patent
Benett et al.

(10) Patent No.: US 6,586,233 B2
(45) Date of Patent: Jul. 1, 2003

(54) CONVECTIVELY DRIVEN PCR THERMAL-CYCLING

(75) Inventors: William J. Benett, Livermore, CA (US); James B. Richards, Danville, CA (US); Fred P. Milanovich, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 145 days.

(21) Appl. No.: 09/802,549

(22) Filed: Mar. 9, 2001

(65) Prior Publication Data

US 2002/0127152 A1 Sep. 12, 2002

(51) Int. Cl.[7] .............................................. C12M 1/36

(52) U.S. Cl. ............................... 435/286.5; 435/287.2; 435/288.7; 422/110

(58) Field of Search .......................... 435/286.5, 287.2, 435/288.7; 422/102, 109, 110, 129; 237/2 A

(56) References Cited

U.S. PATENT DOCUMENTS

| | | | | |
|---|---|---|---|---|
| 5,589,136 A | 12/1996 | Northrup et al. | ........... | 422/102 |
| 5,942,432 A | 8/1999 | Smith et al. | ............. | 435/303.1 |
| 5,958,349 A | 9/1999 | Petersen et al. | ............ | 422/198 |
| 5,972,667 A | 10/1999 | Conia et al. | ............. | 435/173.2 |

FOREIGN PATENT DOCUMENTS

| | | | | |
|---|---|---|---|---|
| EP | 0504435 A1 * | 9/1992 | ............ | C12Q/1/68 |
| WO | WO 99/39005 | 8/1999 | ............ | C12Q/1/68 |

* cited by examiner

*Primary Examiner*—David A. Redding
(74) *Attorney, Agent, or Firm*—Eddie E. Scott; Alan H. Thompson

(57) ABSTRACT

A polymerase chain reaction system provides an upper temperature zone and a lower temperature zone in a fluid sample. Channels set up convection cells in the fluid sample and move the fluid sample repeatedly through the upper and lower temperature zone creating thermal cycling.

18 Claims, 4 Drawing Sheets

CONVECTIVELY DRIVEN PCR THERMAL-CYCLING

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to polymerase chain reactions (PCR), and in particular, to convectively driven PCR thermal-cycling.

2. State of Technology

The polymerase chain reaction (PCR) is widely accepted as the gold standard for identification of biological organisms. PCR is a biochemical method by which the concentration of DNA segments in solution is increased at an exponential rate over time. It is capable of distinguishing between strains of organisms of the same species. PCR typically requires a sample to be repeatedly cycled between temperatures near 95° C. and a temperature below 60° C.

The primary method of PCR thermal cycling has been to heat and cool some form of chamber containing the PCR sample. Conventional PCR thermal cycling is accomplished by placing the PCR sample in a chamber then heating and cooling the chamber and sample to precise temperature set points. The cycling is repeated until PCR amplification is achieved.

PCT publication WO/9939005 titled: "Rapid Thermocycling for Sample Analysis," by the applicant Mayo Foundation for Medical Education and Research, dated Aug. 5, 1999, inventors James, P. Landers, Andreas Huhmer, Robert, P. Oda, and James, R. Craighead provides the following description: "Methods for performing rapid and accurate thermocycling on a sample are disclosed. Use of non-contact heating and cooling sources allows precise temperature control with sharp transitions from one temperature to another to be achieved. A wide range of temperatures can be accomplished according to these methods. In addition, thermocycling can be performed without substantial temperature gradients occurring in the sample. Apparatus for achieving these methods are also disclosed. A method for pumping a sample through microchannels on a microchip using a non-contact heat source is also disclosed."

U.S. Pat. No. 5,942,432 titled: "Apparatus for a Fluid Impingement Thermal Cycler," issued Aug. 24, 1999, to Douglas H. Smith, John Shigeura, and Timothy M. Woudenberg, assigned to The Perkin-Elmer Corporation, provides the following description: "Apparatus are disclosed that thermally cycles samples between at least two temperatures. These apparatus operate by impinging fluid jets onto the outer walls of a sample containing region. Because the impinging fluid jets provide a high heat transfer coefficient between the jet and the sample containing region, the sample containing regions are uniformly cycled between the two temperatures. The heat exchange rate between the jets and the sample regions are substantially uniform."

U.S. Pat. No. 5,972,667 titled: "Method and Apparatus for Activating a Thermo-enzyme Reaction with Electromagnetic Energy," issued to Jerome Conia and Claude Larry Keenan, assigned to Cell Robotics, Inc., provides the following description: "A method and apparatus for activating a thermo-enzyme reaction, such as a polymerase chain reaction or other temperature-sensitive transformation of biological systems are provided. Electromagnetic energy is applied to a target to produce a rapid elevation in the temperature of at least a portion of the target. The electromagnetic energy can be laser energy provided via a laser beam supplied from one or more laser sources. The laser beam can have a wavelength in the infrared range from 750 nm to mm. The source of electromagnetic energy can be used in association with a microscope and/or objective lens to irradiate microscopic targets."

U.S. Pat. No. 5,958,349, for a reaction vessel for heat-exchanging chemical processes by Kurt E. Petersen, William A. McMillan, Gregory T. A. Kovacs, and Steven J. Young, patented Sep. 28, 1999 provides the following description: "A reaction vessel for holding a sample for a heat-exchanging chemical process has two opposing major faces and a plurality of contiguous minor faces joining the major faces to each other. The major and minor faces form an enclosed chamber having a triangular-shaped bottom portion. The ratio of the thermal conductance of the major faces to that of the minor faces is at least 2:1, and the minor faces forming the triangular-shaped bottom portion of the chamber are optically transmissive. The vessel also has a port for introducing a sample into the chamber and a cap for sealing the chamber."

U.S. Pat. No. 5,589,136 for a silicon-based sleeve devices for chemical reactions, by Northrup, et al., patented Dec. 31, 1996, provides the following description: "A silicon-based sleeve type chemical reaction chamber that combines heaters, such as doped polysilicon for heating, and bulk silicon for convection cooling. The reaction chamber combines a critical ratio of silicon and silicon nitride to the volume of material to be heated (e.g., a liquid) in order to provide uniform heating, yet low power requirements. The reaction chamber will also allow the introduction of a secondary tube (e.g., plastic) into the reaction sleeve that contains the reaction mixture thereby alleviating any potential materials incompatibility issues. The reaction chamber may be utilized in any chemical reaction system for synthesis or processing of organic, inorganic, or biochemical reactions, such as the polymerase chain reaction (PCR) and/or other DNA reactions, such as the ligase chain reaction, which are examples of a synthetic, thermal-cycling-based reaction. The reaction chamber may also be used in synthesis instruments, particularly those for DNA amplification and synthesis."

SUMMARY OF THE INVENTION

The present invention provides a polymerase chain reaction system that heats and cools a fluid through convective pumping. The system includes an upper temperature zone and a lower temperature zone. Channels in the polymerase chain reaction system set up convection cells in the fluid and move the fluid repeatedly through the upper temperature zone and the lower temperature zone creating thermal cycling.

Other features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description and by practice of the invention.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
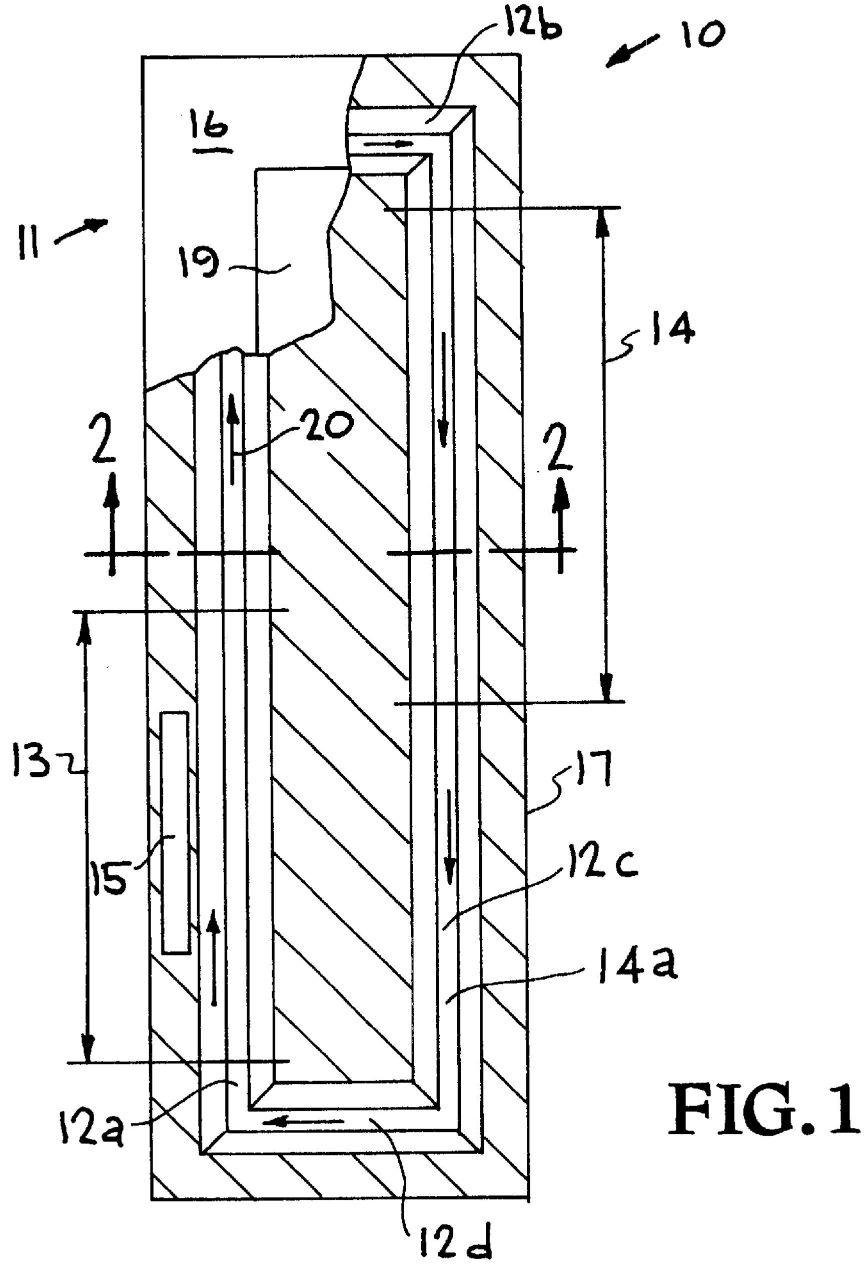
FIG. 1 illustrates an embodiment of a convectively driven PCR thermal-cycling system constructed in accordance with the present invention.

Referring now to the drawings, and in particular to FIG. 1, the structural details and the operation of an embodiment of a convectively driven PCR thermal-cycling system constructed in accordance with the present invention is illustrated. The system is designated generally by the reference numeral 10.

Conventional PCR thermal cycling is an inefficient process because it requires the heating and cooling of material other than the PCR sample itself. There is an increasing need to build smaller more portable PCR systems for use in the field and clinical settings. There is also a growing need to imbed PCR systems in more complex autonomous system for BW/BT agent detection. This embodiment of the present invention provides a convectively driven PCR thermal-cycling system 10. The detailed description of this specific embodiment 10, together with the general description of the invention, serve to explain the principles of the invention.

Structural Elements of the System 10

As show in FIG. 1, a chamber unit 11 is fabricated of a material such as silicon, circuit board fiberglass, ceramic, metal or glass. The chamber unit 11 has channels 12*a*, 12*b*, 12*c*, and 12*d* formed in its walls. The channels 12*a*, 12*b*, 12*c*, and 12*d* create passages for a sample fluid to flow from the "Upper Temperature Zone 13" to the "Lower Temperature Zone 14." Flow is generated by heating specific sections of the channel and creating a convection cell or "convective siphon." A heater 15 is used to heat the upper temperature zone 13. The heater 15 may be a thin film platinum heater for example. It can be applied to either the inside or outside of the chamber unit 11. This type of heater also can be used as a temperature sensor. The arrows show the flow of the sample fluid from the upper temperature zone 13 through the zone of convective driven flow 20 to the lower temperature zone 14. The sample fluid flows from the lower temperature zone through the convective lower temperature zone 14*a* to the upper temperature zone.

Figure 2:
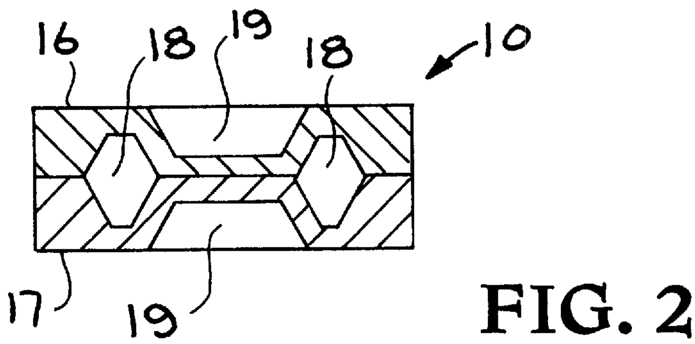
FIG. 2 is a cross sectional view of the PCR thermal-cycling system shown in FIG. 1.

Referring now to FIG. 2 a cross sectional view of the PCR thermal-cycling system is shown. The system 10 is constructed of two chamber halves 16 and 17. The two chamber halves 16 and 17 form sample channels 18. The sample channels 18 are connected together to form the channels 12*a*, 12*b*, 12*c*, and 12*d* shown in FIG. 1. The two chamber halves 16 and 17 include trenches 19 for thermal isolation.

Figure 3:
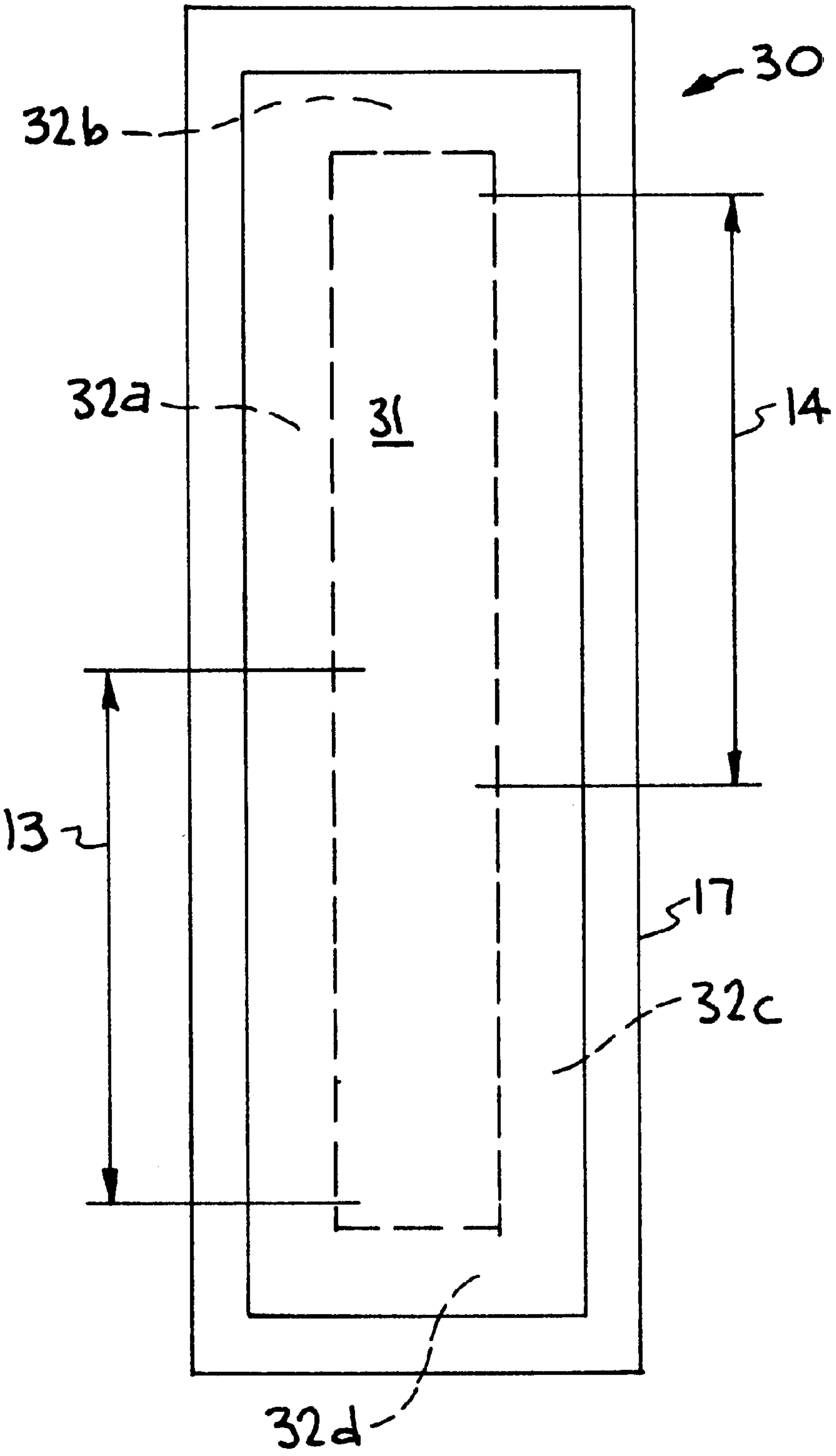
FIG. 3 shows a sample held in a plastic sleeve or pouch.

Referring now to FIG. 3 a sample, generally designated by the reference numeral 30, is shown in a plastic sleeve or pouch 31. The plastic sleeve or pouch 31 will be placed inside the chamber unit 11 shown in FIGS. 1 and 2. The sample 31 will be clamped between the two chamber halves 16 and 17. The plastic sleeve or pouch 31 contains channels 32*a*, 32*b*, 32*c*, and 32*d* that match the channels 12*a*, 12*b*, 12*c*, and 12*d* formed in chamber unit 11.

The system 10 provides a device with precise temperature zones 13 and 14 at the upper and lower temperatures for the PCR reaction. The system 10 is designed so that channels 12*a*, 12*b*, 12*c*, and 12*d* formed in chamber unit 11 will set up convection cells in the fluid that will move the fluid repeatedly through the upper and lower temperature zones thus creating thermal cycling. By moving the fluid through the controlled temperature zones, only the fluid is heated and cooled not the chamber unit. This greatly reduces the heat that needs to be removed from the system and eliminates the need for active cooling. It also simplifies the electronic controls required to operate the system. The present invention eliminates the need for active cooling and greatly simplifies the control systems required for PCR systems. It also increases the power efficiency of the of the PCR system.

Microfabrication Technology Construction of the System 10

The system 10 is constructed using microfabrication technologies. The microfabrication technologies include sputtering, electrodeposition, low-pressure vapor deposition, photolithography, and etching. Microfabricated devices are usually formed on crystalline substrates, such as silicon and gallium arsenide, but may be formed on non-crystalline materials, such as glass or certain polymers. The shapes of crystalline devices can be precisely controlled since etched surfaces are generally crystal planes, and crystalline materials may be bonded by processes such as fusion at elevated temperatures, anodic bonding, or field-assisted methods.

Monolithic microfabrication technology now enables the production of electrical, mechanical, electromechanical, optical, chemical and thermal devices, including pumps, valves, heaters, mixers, and detectors for microliter to nanoliter quantities of gases, liquids, and solids. Also, optical waveguide probes and ultrasonic flexural-wave sensors can now be produced on a microscale. The integration of these microfabricated devices into a single system allows for the batch production of microscale reactor-based analytical instruments. Such integrated microinstruments may be applied to biochemical, inorganic, or organic chemical reactions to perform biomedical and environmental diagnostics, as well as biotechnological processing and detection.

The operation of integrated microinstruments is easily automated, and since the analysis can be performed in situ, contamination is very low. Because of the inherently small sizes of such devices, the heating and cooling can be extremely rapid. These devices have very low power requirement and can be powered by batteries or by electromagnetic, capacitive, inductive or optical coupling. The small volumes and high surface-area to volume ratios of microfabricated reaction instruments provide a high level of control of the parameters of a reaction.

Operation of the System 10

The system 10 consists of chamber unit 11 that will thermally cycle the PCR sample 30. The sample 30 is held in a plastic sleeve or pouch 31 inside the chamber unit 11. It may be clamped between two chamber halves 16 and 17 for better thermal contact. The chamber unit 11 has channels 12 formed in its walls that create passages for the sample fluid to flow. This flow is generated by heating specific sections of the channel 12 and creating a convection cell or "convective siphon."

As the sample 31 is continuously driven by convection through the channels 12*a*, 12*b*, 12*c*, and 12*d* it passes through sections of channel that are temperature controlled to be at the upper and lower temperatures required for the PCR reaction. This continuous flow through the PCR temperature zones effectively thermally cycles the sample.

A variety of heaters and sensors can be used to heat and control temperature. A thin film platinum heater 15, for example, can be applied to either the inside or outside of the chamber unit 11. This type of heater also can be used as a temperature sensor. Windows can be fabricated in the chambers that allow real time optical detection of the PCR reaction using conventional PCR detection techniques.

Important performance criteria for the device are cycling speed, power consumption and size. Fast cycling speeds are desirable for reasons ranging from simple time saving to saving critical minutes when detecting the release of a deadly pathogen. Power consumption is extremely important when designing portable PCR devices, and critical when designing a battery operated instrument. In the absence of active cooling, heating and simmering account for virtually all of the power required. Once again, thermal mass must be minimized. Optical detection is added to the PCR process to make real-time detection possible. This greatly reduces assay time as a sample need not cycle to completion to detect a positive. Also, follow-on processing steps such as gel electrophoresis are not required. The objective is to incorporate real-time detection without sacrificing cycling speed or significantly increasing size or power consumption.

Another Embodiment of a Convectively Driven PCR Thermal-Cycling System 40

Figure 4:
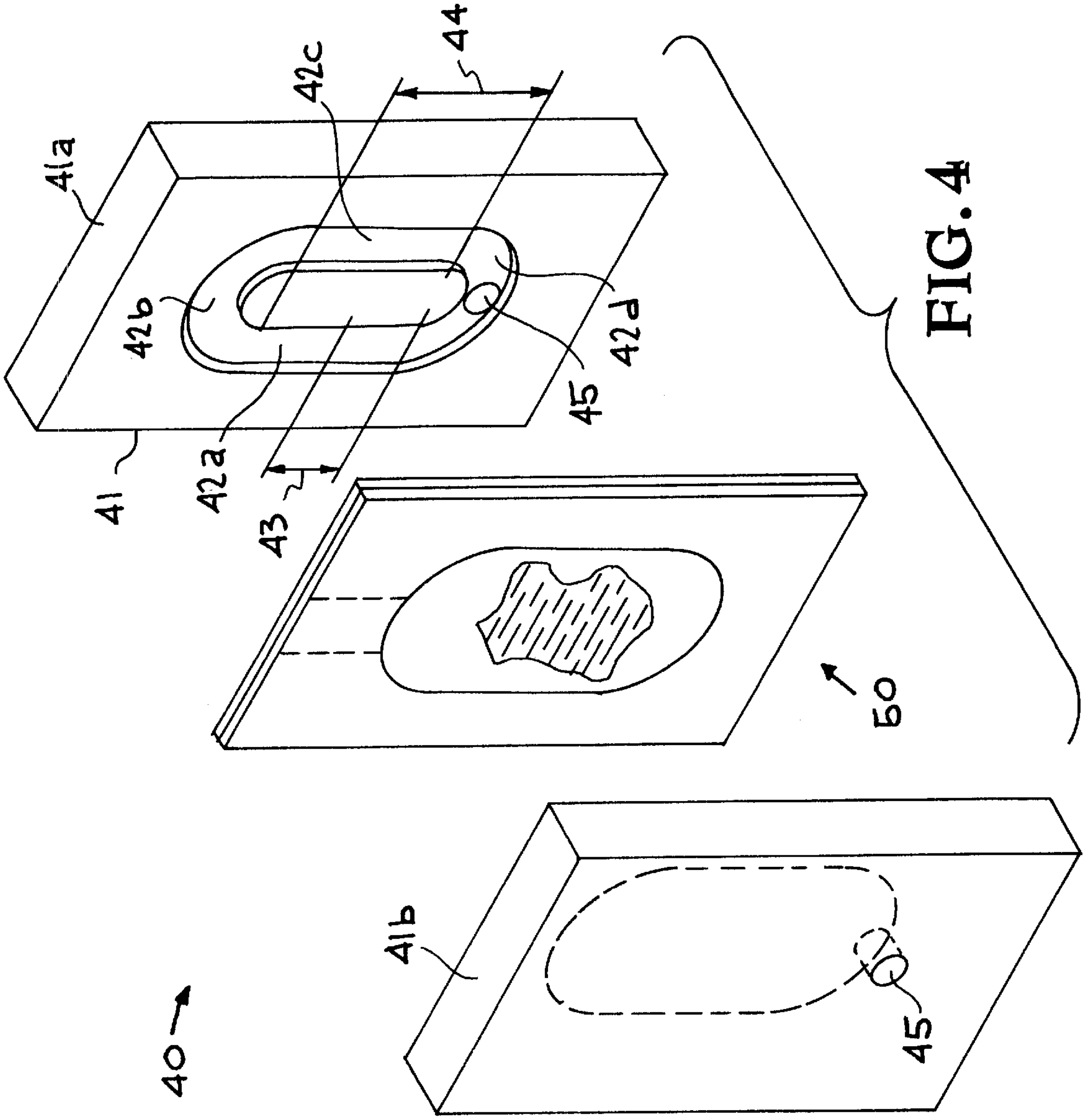
FIG. 4 illustrates another embodiment of a convectively driven PCR thermal-cycling system constructed in accordance with the present invention.

Referring again to the drawings, and in particular to FIG. 4, the structural details and the operation of another embodiment of a convectively driven PCR thermal-cycling system constructed in accordance with the present invention is illustrated. The system is designated generally by the reference numeral 40. The detailed description of this specific embodiment 40, together with the general description of the invention, serve to explain the principles of the invention.

Structural Elements of the System 40

As show in FIG. 4, a chamber unit 41 is fabricated of circuit board material. The system can be constructed of materials such as circuit board fiberglass, silicon, ceramics, metal, or glass. Advantages of using circuit board fiberglass are the fact that it is not as thermally conductive as the other materials and the heating is more efficiently applied to the sample rather than being conducted to surrounding materials. Circuit board material is readily available and the technology of producing and working with circuit board material is highly developed. Circuit board material provides lower cost techniques for fabrication. Printed circuit board technology incorporates photolithography, metal etching, numerically controlled machining, and layering technologies to produce the desired device.

The chamber unit includes two chamber halves 41*a* and 41*b*. A sample container 50 is located between the two chamber halves 41*a* and 41*b*. The chamber unit 41 has channels 42*a*, 42*b*, 42*c*, and 42*d* formed in its walls. The channels 42*a*, 42*b*, 42*c*, and 42*d* create passages for a sample fluid to flow from the "Upper Temperature Zone 43" to the "Lower Temperature Zone 44." Flow is generated by heating specific sections of the channel 11 and creating a convection cell or "convective siphon." A heater is embedded in upper temperature zone 43 and is used to heat the fluid in the upper temperature zone 43. The heater may be a thin film platinum heater for example. It can be applied to either the inside or outside of the chamber unit 41. This type of heater also can be used as a temperature sensor. The sample fluid flows from the upper temperature zone 43 through a zone of convective driven flow to the lower temperature zone 44 and from the lower temperature zone 44 through a convective lower temperature zone back to the upper temperature zone 43. An optical detection window 45 proved access to the sample for optical sensors and detectors.

Figure 5:
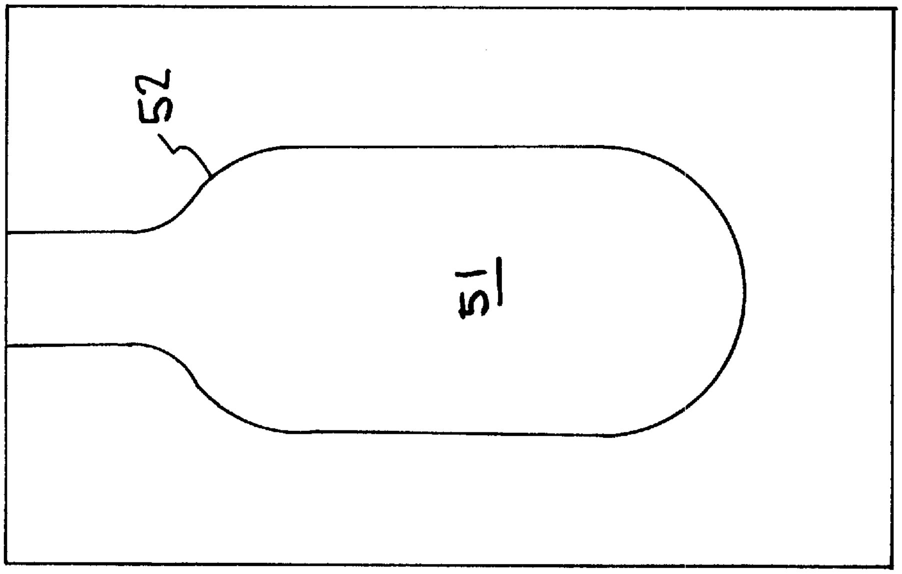
FIG. 5 shows a sample held in a pouch.

Referring now to FIG. 5 a sample container, generally designated by the reference numeral 50 is shown. The sample is contained in a pouch 51. The pouch 51 is formed from a plastic type material 53. The seam 52 defines the pouch area. The sample container 50 is in effect like a Zip Lock plastic bag with the area outside the pouch area void of air, sample, liquid, etc. The sample container 50 will be placed inside the chamber unit 41 shown in FIG. 4. The sample container 50 will be clamped between the two chamber halves 41*a* and 41*b*. When the sample container is clamped between the two chamber halves 41*a* and 41*b* the pouch 51 compressed into the channels 42*a*, 42*b*, 42*c*, and 42*d*. The center of the pouch is squeezed together forcing the sample entirely into channels 42*a*, 42*b*, 42*c*, and 42*d*.

Figure 6:
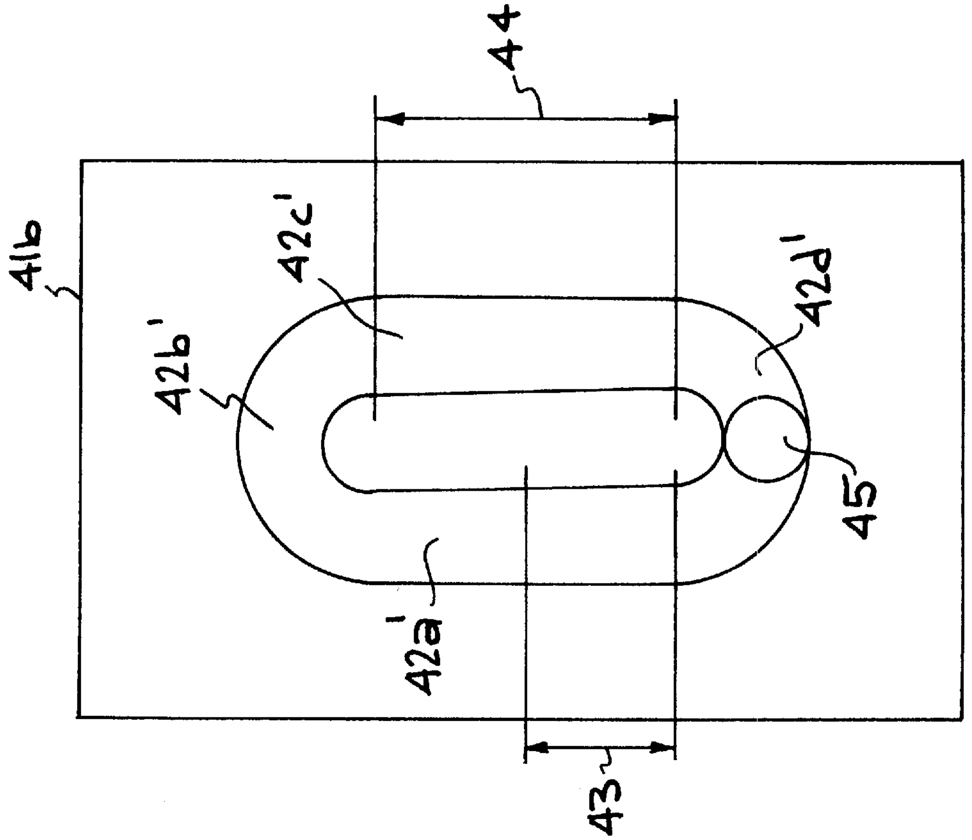
FIG. 6 shows one half of a convectively driven PCR thermal-cycling chamber unit illustrating the temperature controlled zones.

Referring now to FIG. 6 the chamber half 41*b* is shown. The chamber 41*b* includes channels 42*a*', 42*b*', 42*c*', and 42*d*'. The channels 42*a*', 42*b*', 42*c*', and 42*d*' when matched with the channels 42*a*, 42*b*, 42*c*, and 42*d* in chamber half 41*a* create passages for a sample fluid to flow from the "Upper Temperature Zone 43" to the "Lower Temperature Zone 44." Flow is generated by heating specific sections of the channel 41 and creating a convection cell or "convective siphon." An optical detection window 45 proved access to the sample for optical sensors and detectors.

The system 40 provides a device with precise temperature zones 43 and 44 at the upper and lower temperatures for the PCR reaction. The system 40 is designed so that the channels formed in chamber unit 41 will set up convection cells in the fluid that will move the fluid repeatedly through the upper and lower temperature zones thus creating thermal cycling. By moving the fluid through the controlled temperature zones only the fluid is heated and cooled not the chamber unit. This greatly reduces the heat that needs to be removed from the system and eliminates the need for active cooling. It also simplifies the electronic controls required to operate the system. The present invention eliminates the need for active cooling and greatly simplifies the control systems required for PCR systems. It also increases the power efficiency of the of the PCR system.

Printed Circuit Board Technology Construction of the System 40

The system 40 is constructed using printed circuit board technologies. As show in FIGS. 4, 5, and 6, the system 40 can be constructed of printed circuit board materials. Circuit board material provides lower cost techniques for fabrication. Printed circuit board technology incorporates photolithography, metal etching, numerically controlled machining, and layering technologies to produce the system 40. Advantages of using circuit board material are the fact that it is not as thermally conductive as the other materials and the heating is more efficiently applied to the sample rather than being conducted to surrounding materials. Circuit board material is readily available and the technology of producing and working with circuit board material is highly developed.

Operation of the System 40

The system 40 consists of chamber unit 41 that will thermally cycle the PCR sample. The sample is held in pouch container 50 inside the chamber unit 41. It is clamped between the two chamber halves 41*a* and 41*b*. The chamber unit 41 has channels formed in its walls that create passages for the sample fluid to flow. This flow is generated by heating specific sections of the channel and creating a convection cell or "convective siphon."

As the sample is continuously driven by convection through the channels it passes through sections of channel that are temperature controlled to be at the upper and lower temperatures required for the PCR reaction. This continuous flow through the PCR temperature zones effectively thermally cycles the sample.

A variety of heaters and sensors can be used to heat and control temperature. A thin film platinum heater can be applied to either the inside or outside of the chamber unit 41. This type of heater also can be used as a temperature sensor. The optical detection window 45 is fabricated in the chamber unit 41 and allows real time optical detection of the PCR reaction using conventional PCR detection techniques.

Important performance criteria for the device are cycling speed, power consumption and size. Fast cycling speeds are desirable for reasons ranging from simple time saving to saving critical minutes when detecting the release of a deadly pathogen. Power consumption is extremely important when designing portable PCR devices, and critical when designing a battery operated instrument. In the absence of active cooling, heating and simmering account for virtually all of the power required. Once again, thermal mass must be minimized. Optical detection is added to the PCR process to make real-time detection possible. This greatly reduces assay time as a sample need not cycle to completion to detect a positive. Also, follow-on processing steps such as gel electrophoresis are not required. The objective is to incorporate real-time detection without sacrificing cycling speed or significantly increasing size or power consumption.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A PCR apparatus that moves a sample through thermal cycling, comprising:

an upper temperature zone, a lower temperature zone, a chamber unit, wherein said upper temperature zone and said lower temperature zone are contained within said chamber unit and wherein said chamber unit has a multiplicity of sections that fit together to form said chamber unit and wherein said sample is contained in a container located within said multiplicity of sections that fit together to form said chamber unit, and channels in said PCR apparatus operatively connected to said upper temperature zone and said lower temperature zone adapted to set up convection cells in said sample that will move said sample repeatedly through said upper temperature zone and said lower temperature zone creating thermal cycling.

2. The PCR apparatus of claim 1 wherein said container includes a pouch for containing said sample.

3. The PCR apparatus of claim 1 wherein said chamber unit is printed circuit board material.

4. The PCR apparatus of claim 1 wherein said chamber unit is printed circuit board fiberglass.

5. The PCR apparatus of claim 1 wherein said chamber unit is silicon.

6. The PCR apparatus of claim 1 wherein said chamber unit is fabricated of silicon, circuit board fiberglass, ceramic, metal, or glass.

7. The PCR apparatus of claim 1 including an optical detection window in said chamber unit.

8. The PCR apparatus of claim 1 including a heater within said chamber unit for heating said upper temperature zone.

9. The PCR apparatus of claim 1 including an optical detection window in said chamber unit.

10. A polymerase chain reaction method, comprising:

providing an upper temperature zone, providing a lower temperature zone, and allowing a sample to move through said upper temperature zone and said lower temperature zone creating a convective siphon that sets up convection cells in said sample and moves the sample repeatedly through said upper and lower temperature zones creating thermal cycling, wherein said upper temperature zone is heated by a heater, and including using an optical detection system for optical detection.

11. A method of constructing a PCR apparatus, comprising:

constructing a multiplicity of sections that fit together to form a chamber unit having an upper temperature zone, a lower temperature zone, and channels in said chamber unit operatively connected to said upper temperature zone and said lower temperature zone adapted to set up convection cells in said sample that will move said sample repeatedly through said upper temperature zone and said lower temperature zone creating thermal cycling, wherein said chamber unit is constructed of two sections and said two sections are fitted together to form said chamber unit.

12. The method of constructing a PCR apparatus of claim 11 including providing a sample container in said chamber unit.

13. The method of constructing a PCR apparatus of claim 12 wherein said sample is contained in a container located within said multiplicity of sections that fit together to form said chamber unit.

14. The method of constructing a PCR apparatus of claim 12 wherein said container is formed as a pouch for containing said sample.

15. The method of constructing a PCR apparatus of claim 11 wherein at least some of said multiplicity of sections that fit together to form a chamber unit are constructed of printed circuit board material.

16. The method of constructing a PCR apparatus of claim 11 wherein at least some of said multiplicity of sections that fit together to form a chamber unit are constructed of printed circuit board fiberglass.

17. The method of constructing a PCR apparatus of claim 11 wherein at least some of said multiplicity of sections that fit together to form a chamber unit are constructed of silicon.

18. The method of constructing a PCR apparatus of claim 11 wherein at least some of said multiplicity of sections that fit together to form a chamber unit are constructed of silicon, circuit board fiberglass, ceramic, metal, or glass.

* * * * *